United States Patent [19]
McLaren

[11] Patent Number: 5,100,405
[45] Date of Patent: Mar. 31, 1992

[54] LOCKING CAP FOR MEDICAL IMPLANTS

[76] Inventor: Alexander C. McLaren, 5736 N. 33rd Pl., Paradise Valley, Calif. 85253

[21] Appl. No.: 580,106

[22] Filed: Sep. 7, 1990

[51] Int. Cl.$^5$ .............................................. A61B 17/56
[52] U.S. Cl. ........................................ 606/72; 606/73
[58] Field of Search ............... 606/65, 66, 62, 63, 606/72, 73, 59; 403/299-308

[56] References Cited

U.S. PATENT DOCUMENTS

| | | | |
|---|---|---|---|
| 146,023 | 12/1873 | Russell | 411/415 |
| 470,238 | 3/1892 | Goodman | 403/299 |
| 470,238 | 3/1892 | Goodman | 411/243 |
| 1,898,087 | 2/1933 | Fullman | 52/221 |
| 1,984,026 | 12/1934 | Little | 403/299 |
| 2,059,175 | 10/1936 | Myracle | 403/299 |
| 2,059,175 | 10/1936 | Myracle | 403/299 |
| 2,801,631 | 8/1957 | Charnley | 606/65 |
| 3,447,821 | 6/1969 | Bochory | 403/308 |
| 3,530,854 | 9/1970 | Kearney | 606/67 |
| 3,900,220 | 8/1975 | Buchser | 403/299 |
| 4,175,555 | 11/1979 | Herbert | 606/73 |
| 4,306,468 | 12/1981 | Bolgert | 403/299 |
| 4,484,570 | 11/1984 | Sutter et al. | 606/72 |
| 4,500,224 | 2/1985 | Ewing | 403/299 |
| 4,800,873 | 1/1989 | Audell | 606/62 |
| 4,875,474 | 10/1989 | Border | 606/63 |
| 4,875,475 | 10/1989 | Comte et al. | 606/64 |
| 4,927,421 | 5/1990 | Goble | 606/73 |
| 4,927,421 | 5/1990 | Goble et al. | 606/73 |

OTHER PUBLICATIONS

Data Sheets for Herbert TM Bone Screw [See U.S. Pat. No. 4,175,555].

Primary Examiner—Robert A. Hafer
Assistant Examiner—Michael Brown
Attorney, Agent, or Firm—Limbach & Limbach

[57] ABSTRACT

A locking cap for anchoring an implanted medical device within a bone (such as an intramedullary fixation rod) has a cylindrical, helically threaded body, a socket concentrically disposed in one end, and an interface for cooperating with a driving tool, such as a wrench or screwdriver. Once a device such as an intramedullary fixation rod has been implanted within a bone, the locking cap is implanted by being threaded into the bone with a driving tool, its socket engaging the near end of the device. The socket of the locking cap can be smooth, or it can be threaded so as to thread onto the near end of the device as the cap is threaded into the bone. If threaded, the pitch of the cap's outer threads can exceed the pitch of the inner threads so that the cap advances into the bone more quickly than it advances onto the end of the device. Alternatively, the inner thread pitch can exceed, or equal, the outer thread pitch so that the cap advances into the bone more slowly than, or at the same rate as, it advances onto the end of the device, respectively.

44 Claims, 2 Drawing Sheets

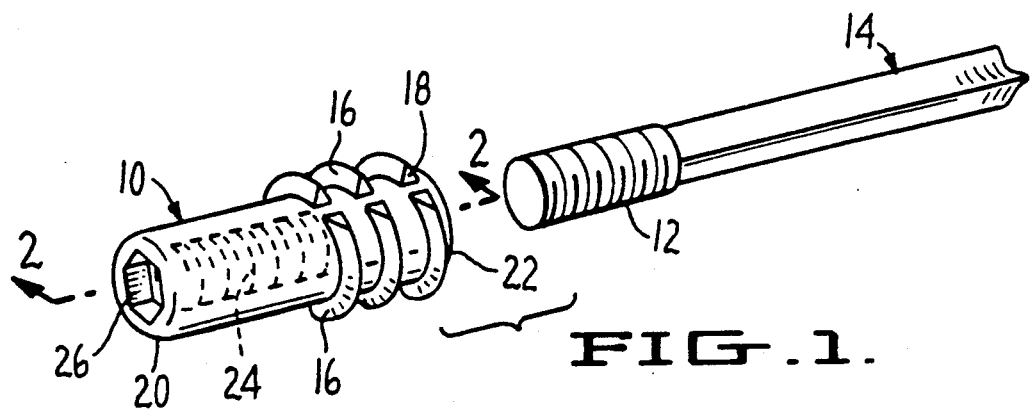
FIG. 1.
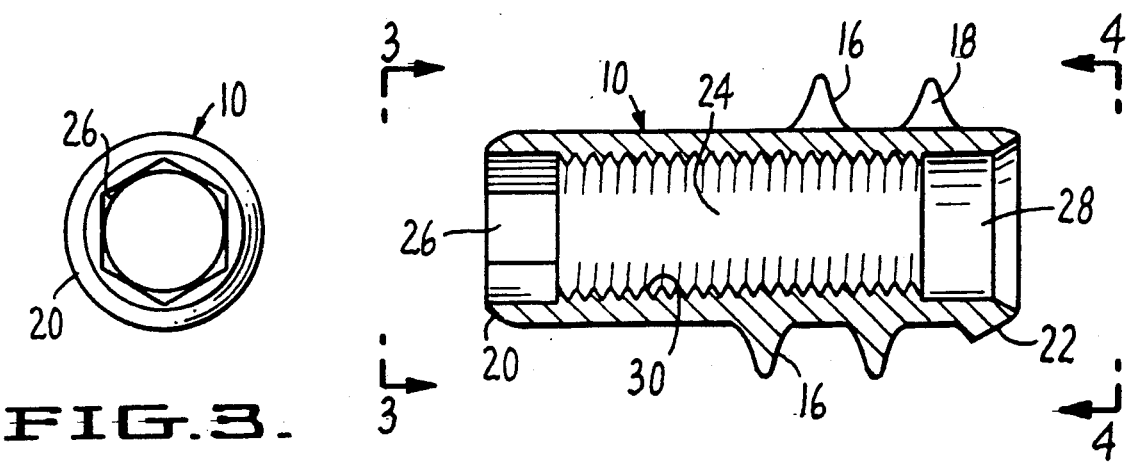
FIG. 3.
FIG. 2.
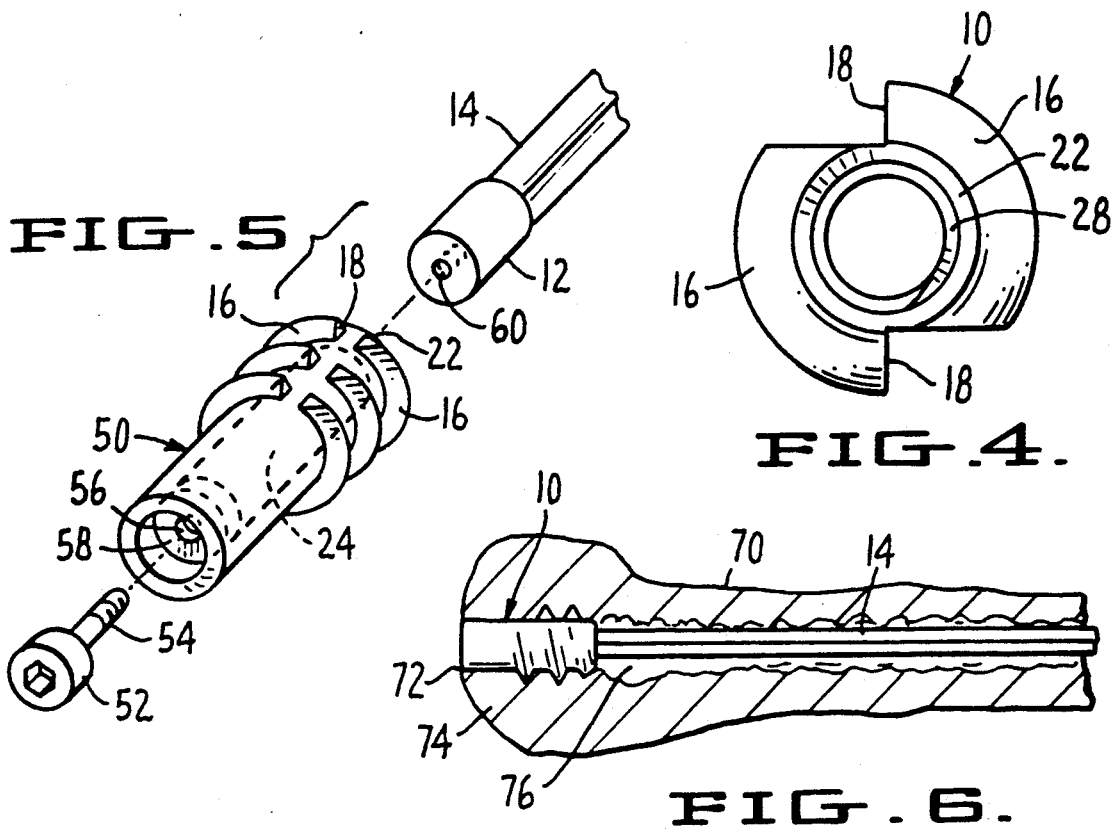
FIG. 5.
FIG. 4.
FIG. 6.

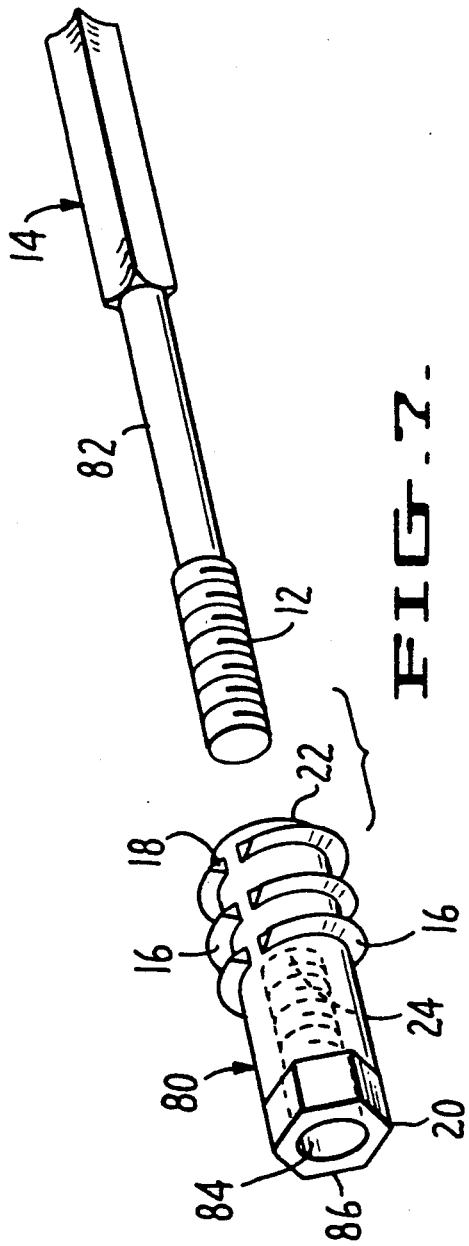
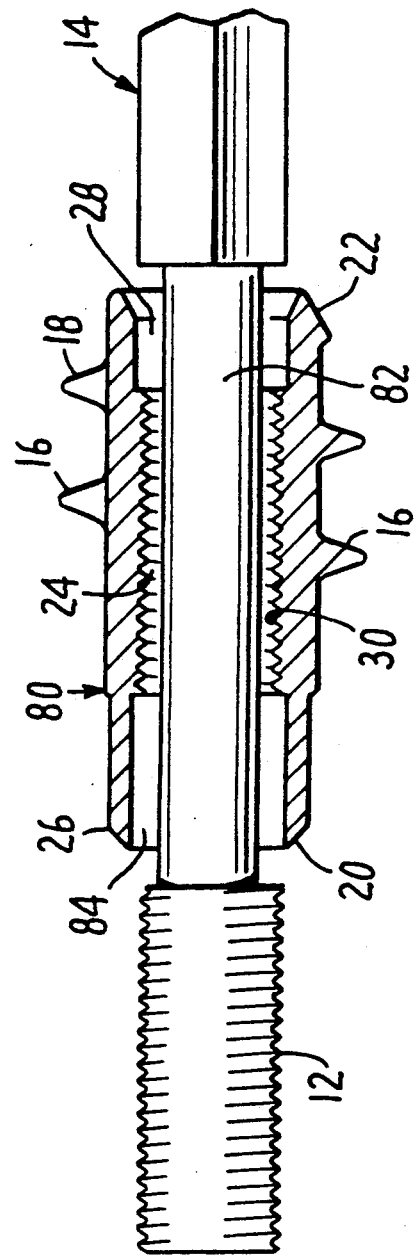

LOCKING CAP FOR MEDICAL IMPLANTS

BACKGROUND OF THE INVENTION

1. Field of the Invention

The present invention relates to medical implants, and in particular, to threaded devices used for anchoring medical implants.

2. Description of the Related Art

To be effective, medical implants, such as intramedullary fixation rods, must be securely positioned and remain stable once installed. For example, once a long bone fracture has been reduced and an intramedullary fixation rod has been installed, axial, rotational and angular stability of the rod must be maintained. If not, the benefits otherwise afforded by the use of the fixation rod will not be fully realized. To date, several different means have been used to anchor fixation rods to provide the requisite stabilities.

One type of anchoring device uses a pin installed transversely within the bone. For example, see U.S. Pat. Nos. 3,763,855 and 4,212,294. A transverse hole is drilled through the cortex of the bone. A pin having a transverse threaded aperture within its shaft is installed and the aperture is aligned with the medullary canal of the bone. As an intramedullary fixation rod is installed, it is threaded through the pin aperture. The threaded engagement of the pin and rod provides axial stability for the rod. A disadvantage of this type of anchoring device is the risk of additional trauma imposed upon the patient by the transverse hole in the bone required for the pin.

Another type of anchoring device also requires transverse holes for the installation of pins or screws. Some types of intramedullary fixation rods are fabricated with longitudinal and transverse holes or slots. When the fixation rod is installed, transverse holes are drilled through the cortex of the bone in alignment with the holes o slots in the rod. Pins, screws or bolts are then installed within these transverse holes and through the holes or slots of the rod. The holes in the fixation rod may be threaded to receive screws or bolts, or sometimes brackets or plates are used on the outside of the bone in conjunction with the screws or bolts. For example, see U.S. Pat. 4,135,507 and 3,709,218. As with the apertured transverse pin described above, a disadvantage of this type of anchoring device is the risk of additional trauma imposed upon the patient.

These types of anchoring devices have the further disadvantage of making the surgery for their installation and removal more complex and time-consuming. With so many pins, screws, plates, etc. to install, the surgeon and patient both must spend that much more time in surgery. And for the surgeon in particular, the extra operational steps needed for installing all that hardware can be quite time consuming.

Still another type of anchoring device for a bone fixation rod does not use transverse pins, screws or bolts. Instead, the distal end of the fixation rod is equipped with radially expanding projections. For example, see U.S. Pat. Nos. 3,678,925 and 3,716,051. Once the rod is installed, the projections are caused to radially expand within the shaft (e.g. medullary canal) into which the rod has been installed. The expanding projections thereby provide a tight friction fit for the rod within the bone.

This type of anchoring device can have two disadvantages. First, the fixation rod is more complicated with the radially expandable projections and the mechanical coupling necessary to remotely activate those projections. Second, the expanding projections can cause the rod to become incarcerated within the bone, making extraction difficult.

Yet another type of anchoring device for an intramedullary fixation rod consists of a form of lag bolt. A hollow fixation rod is used with this device. For example, see U.S. Pat. Nos. 3,530,854 and 3,990,438. After the rod has been installed, the bolt is passed longitudinally through the hollow core of the rod. The threaded portion of the screw protrudes from the distal end of the rod and is threaded into the bone until the head of the lag screw engages some form of blocking structure within the fixation rod.

This type of anchoring device can have two disadvantages. First, installation of the lag screw requires an additional hole within the bone at the distal end of the fixation rod. This can introduce risks of undesirable stress and trauma within the bone. Second, since the fixation rod must be hollow, and the lag screw must be sufficiently large to be effective in grabbing into the bone when threaded therein, the fixation rod diameter must be relatively large. This will limit the use of such a rod to only large bones.

Therefore, it can be seen that an alternative anchoring or locking mechanism for bone fixation rods o other types of medical implants is desirable. In particular, it would be desirable to have such an alternative device which requires no difficult or time-consuming drilling of additional holes in the bone or installation of extra hardware, nor any complex mechanical features such as radially expanding projections which can cause undesirable incarceration of the device.

SUMMARY OF THE INVENTION

A medical implant anchoring or locking cap in accordance with the present invention requires no additional or special installation holes or hardware, nor the use of specialized or complicated medical implants (e.g. fixation rod assemblies).

The locking cap of the present invention has a cylindrical helically threaded member with a proximal driving end and a distal driven end. It has a tool interface in its proximal driving end and a socket concentrically disposed within its distal driven end for receiving a proximal end of an implanted medical device. After a medical device, such as an intramedullary fixation rod, has been implanted (e.g. within the medullary canal of a bone), the locking cap of the present invention is threaded into the bone in the same hole through which the medical device was installed. The locking cap's outer helical threads have cutting flutes which make the locking cap self-threading with respect to the bone.

The socket in the distal driven end of the locking cap engages a proximal end of the medical device. If the proximal end of the medical device is threaded, the socket of the locking cap can be threaded so as to engage and mate with the threads of the device. The locking cap's proximal tool interface can be a receptacle for engaging a wrench or a screwdriver tip.

If the locking cap's socket is threaded to engage a threaded medical device, such as a fixation rod with a threaded end, the locking cap's outer helical threads preferably have a like-handed thread pitch which is greater than the thread pitch of the locking cap's inner socket threads (e.g. at least 2:1). Such a thread pitch relationship causes the locking cap to thread into the bone at a faster rate than it threads onto the medical device end. Therefore, as the locking cap advances into the bone, axial advancement of the medical device is induced. However, depending upon the desired application, the outer and inner thread pitches can be opposite-handed. Further, the outer thread pitch can be less than or equal to the inner thread pitch (e.g. less than or equal to 1:1), as desired.

Alternatively, the locking cap of the present invention can have a medical device receiving socket within its distal driven end which is not threaded, and merely receives the proximal end of the medical device. An access hole connecting the proximal driving end of the locking cap to the socket allows a locking screw to be inserted to engage the proximal end of the medical device, thereby coupling the locking cap and medical device together.

Thus, once the locking cap is installed, the implanted medical device with which it is engaged is anchored. In the case of an intramedullary fixation rod, the cap provides the rod with axial stability, minimizing any longitudinal movement of the rod within the medullary canal. Furthermore, removal of the fixation rod is facilitated. By backing the locking cap out from the bone, the rod is also withdrawn. No special tool is needed to initiate the removal of the rod.

These and other objectives, features and advantages of the present invention will be understood upon consideration of the following detailed description of the invention and the accompanying drawings.

BRIEF DESCRIPTION OF THE DRAWINGS

Throughout the figures, corresponding elements are designated with similar numerals.

FIG. 1 illustrates a perspective view of a locking cap in accordance with the present invention in alignment with the proximal end of an intramedullary fixation rod for engagement therewith.

FIG. 2 illustrates a cut-away elevational view taken on the plane designated by line 2—2 in FIG. 1.

FIG. 3 illustrates a plan view taken on the plane designated by line 3—3 in FIG. 2.

FIG. 4 illustrates a plan view taken on the plane designated by line 4—4 in FIG. 2.

FIG. 5 illustrates a perspective view of an alternative embodiment of the present invention in alignment with an intramedullary fixation rod for engagement therewith.

FIG. 6 illustrates a cut-away elevational view of an installed intramedullary fixation rod anchored within a bone with a locking cap of the present invention.

FIG. 7 illustrates a perspective view of an alternative embodiment of the present invention in alignment with the proximal end of an intramedullary fixation rod for engagement therewith.

FIG. 8 illustrates a cut-away elevational view of the locking cap and intramedullary fixation rod of FIG. 7 in mutual engagement.

DETAILED DESCRIPTION OF THE INVENTION

Referring to FIG. 1, a locking cap 10 in accordance with a preferred embodiment of the present invention is shown in axial alignment with a proximal end 12 of an intramedullary fixation rod 14. Disposed about the cylindrical periphery of the cap 10 are helical outer threads 16. The outer threads 16 have cutting flutes 18. Extending longitudinally and concentrically from the proximal end 20 to the distal end 22 within the cap 10 is a like-handed threaded shaft 24. At the distal end 22 of the cap 10 the threaded shaft 24 serves as a socket for engaging the threaded proximal end 12 of the rod 14. At the proximal end 21 of the cap 10 is a tool interface 26, which for a preferred embodiment, is a hexagonal socket for receiving a hexagonal wrench tip.

Referring to FIG. 2, the socket 28 formed at the junction of the threaded shaft 24 and distal end 22 of the cap 10 can be better seen. An outer portion of the socket 28 is smooth, i.e. not threaded, to facilitate engagement with the threaded end 12 of the rod 14, as described above. Once the threaded end 12 of the rod 14 has engaged the socket 28, its threads will mesh with the threads 30 within the shaft 24 deeper within the socket 28 as the cap 10 is rotated.

The tool interface 26 at the proximal end 20 of the cap 10 facilitates rotation of the cap 10 during installation. For the embodiment illustrated, the tip of a hexagonal wrench (not shown) is inserted into the tool interface 26 and rotated. As seen in FIG. 3, the tool interface 26 is substantially concentric with the longitudinal axis of the cap 10.

Referring to FIG. 4, it can be seen that the cutting flutes 18 within the helical outer threads 16 are provided substantially diagonally opposite one another about the cap 10. The cutting flutes 18 provide the cap 10 with a self-threading capability to facilitate its installation (discussed more fully below).

It should be understood that the concentric shaft 245 within the cap 10 need not necessarily connect eh proximal 20 and distal 22 ends of the cap 10. In other words, the shaft 24 need not extend the full length of the cap 10, but rather, can extends as deeply into the cap 10 from the distal end 22 as desired.

Furthermore, the tool interface 26 need not necessarily be a hexagonal socket for accepting a hexagonal wrench tip. The tool interface for either cap embodiment 10, 50 can be any type adapted to cooperatively engage a driving tool, such as a wrench (e.g. Torx ®, socket, etc.) or screwdriver.

An alternative preferred embodiment of the present invention is a cap 50 as illustrate in FIG. 5. This alternative cap 50, just as in the embodiment in FIG. 1, has helical outer threads 16 with cutting flutes 18 and a concentric internal shaft 24. In this embodiment, the internal shaft 24 is smooth-bored, i.e. non-threaded, to cooperatively engage the end 12 of an intramedullary fixation rod 14. When this cap is engaged with the rod 14, it is secured thereto via a set screw 52. The set screw 52 has a threaded tip 54 which is inserted through a hole 56 in a concentric shoulder 58 within the internal shaft 24. The threads 54 engage a similarly threaded hole 60 within the end 12 of the rod 14. Tightening the set screw 52 securely couples the cap 50 to the rod 14.

Although not shown in FIG. 5, it Will be understood that the proximal end 20 of the alternative cap 50 can be provided with a tool interface as desired. For example, a hexagonal socket can be used as in the cap 10 of FIG. 1.

Referring to FIG. 6, a locking cap 10 in accordance with the present invention is shown anchoring an intramedullary fixation rod 14 within a bone 70. An important benefit of the present invention is immediately realized. No holes in addition to that needed to implant the fixation rod 14 are required. Rather, the locking cap 10, 50 of the present invention uses the same hole, and provides the necessary axial stability for the rod 14. Therefore, no difficult or time-consuming drilling of additional holes is needed.

As is well known in the art, implantation of an intramedullary fixation rod 14 into a broken long bone 70 requires the drilling of an insertion hole 72 through the cortex 74. Once the rod 14 has been implanted within the medullary canal 76, it should be anchored to assure its stability. The cap o of the present invention provides the requisite stability.

When installing the rod 14, its distal end (not shown) is inserted first and the rod 14 is driven into the medullary canal 76 through the use of an appropriate tool (e.g. slap-hammer) coupled to the rod's proximal end 12. The rod 14 is inserted up to the point where its proximal end 12 is substantially within the installation hole 72. At this point, the installation tool can be removed and the cap 10 installed.

For the preferred cap embodiment 10 of FIG. 1, the cap's socket 28 engages the rod's proximal end 12. As the cap 10 is rotated, the threads of the rod end 12 mesh with the threads 30 of the shaft 24 deeper within the cap's socket 28. After the desired number of threads have meshed, the cutting flutes 18 of the outer threads 16 engage the cortex 74 of the bone 70 to begin the self-threading of the cap 10 therein, and thereby fasten the cap 10 to the bone 70. The higher thread pitch of the outer threads 16 cause the cap 10 to advance more rapidly into the cortex 74, relative to the advancement of the cap 10 onto the rod 14.

Due to the engagement of the cap 10 with the rod 14, the advancement of the cap 10 into the cortex 74 causes the rod 14 to advance axially within the medullary canal 76. Once the cap 10 has been threaded into the cortex 74 as far as desired, the cap 10, and therefore the fixation rod 14, are axially anchored.

For the alternative cap embodiment 50 of FIG. 5, the cap's socket 28 also engages the rod's proximal end 12. When the shoulder 58 in the shaft 24 is sufficiently close to the rod's proximal end 12, the cap 50 can be coupled to the rod 14 via the set screw 52. After engaging the desired number of screw threads 54 in the rod's threaded hole 60, the cutting flutes 18 of the cap's outer threads 16 are engaged with the cortex 74 of the bone 70 to begin the self-threading of the cap 50 therein. The pitch of the outer threads 16 causes the cap 50 to advance into the cortex 74.

This engagement of either embodiment 10, 50 of the cap with the rod 14 is further beneficial in that it makes removal of the rod 14 easier. By threading the cap back out from the cortex 74, the rod 14 is withdrawn from the medullary canal 76. Once the cap has been backed out completely from the hole 72, e.g. When all outer threads 16 are disengaged from the cortex 74, the cap can be disengaged from the rod 14. The appropriate tool (e.g. slap-hammer) can then be used to complete the removal of the rod 14.

A further alternative preferred embodiment of the present invention is a cap 80 as illustrated in FIGS. 7 and 8. This alternative cap 80, just as in the embodiment in FIG. 1, has helical outer threads 16 with cutting flutes 18 and a concentric internal shaft 24. In this embodiment, the internal shaft 24 extends from the cap's proximal end 20 to its distal end 22, thereby connecting the socket 28 to an outlet 84. The tool interface 86 is configured to cooperatively engage a driving tool, e.g. a wrench (not shown), which couples to an outer portion of the cap 80 (rather than into a receptacle 26 as seen in the cap 10 of FIG. 1).

As with the cap 10 of FIG. 1, this cap 80 threads onto the rod end 12. However, the cap's proximal end 20 has an outlet 84 designed to allow the rod end 12 to extend or protrude. Thus, the cap 80 can be threaded all the way down and beyond the threads of the rod end 12, and slide over the smooth, e.g. non-threaded, portion 82 of the rod 14, as shown in FIG. 8. This cap embodiment so can be desirable where the cap so must be threaded into a bone (as shown in FIG. 6 and discussed above), but the rod 14 is not implanted deeply enough to cause the threaded rod end 12 to be sufficiently recessed within its installation hole.

The locking cap of the present invention can be fabricated by methods well known in the art from a number of physiologically compatible materials. Such materials include, without limitation, cobalt chrome, titanium, stainless steel (e.g. surgical grade 316L), ceramic materials, resorbable materials (e.g. polylactic acid), carbon fiber-polysulfone, or other composite materials.

Typical approximate ranges for dimensions of the locking cap are 3.5–7.5 millimeters (mm) for the outer diameter, exclusive of the outer threads 16, and 2.0–6.0 mm for the inner diameter of the shaft 24. However, it will be understood that for smaller or larger implants, or for smaller or larger bone masses into which the cap is to be installed, the outer and inner diameters can vary as desired. For example, for anchoring an implant in a small bone, the diameters can reach as low as approximately 1 mm, while for anchoring an implant in a larger bone, such as a hip bone, the diameters can reach as high as approximately 25 mm.

It can be seen from the foregoing discussion that a cap in accordance with the present invention benefits both surgeon and patient. Fewer holes and less hardware are needed for implanting, anchoring and removing a medical device, translating to less work and less time in surgery.

It should be understood that the respective thread pitches of the outer threads 16 and inner threads 30 of the cap embodiments 10, 80 of FIGS. 1 and 7 can vary as desired. If the thread pitch of the outer threads 16 is greater than the thread pitch of the inner threads 30 (e.g. at least 2:1), the cap will advance more rapidly into the cortex 74 than the cap will advance onto the rod end 12. If the respective thread pitches are approximately equal, the respective rates of advancement will also be approximately equal.

It should be further understood that, depending upon the desired application, the thread pitch of the inner threads 30 can be greater than the thread pitch of the outer threads 16, thereby causing the cap to advance more slowly into the cortex 74 than onto the rod end 12. Moreover, depending upon the desired application, the outer 16 and inner 30 threads can be other than likehanded. For example, the outer threads 16 can be right-handed while the inner threads 30 are left-handed, or vice versa.

Various alternatives to the embodiments of the present invention described herein can be employed in practicing the present invention. It is intended that the following claims define the scope of the present invention, and that structures and methods within the scope of these claims and their equivalents be covered thereby.

What is claimed is:

1. A locking cap for driving into a bone to lock an implanted medical device within a bone by engaging a proximal end of said device and fastening said cap to a bone, comprising:

an elongate cylindrical member having helical outer threads about its cylindrical periphery, a driving end and a longitudinally opposed driven end, said outer threads having an outer thread pitch;

an elongate cylindrical socket for receiving said proximal end of said medical device, said socket being concentrically disposed within said cylindrical member driven end and said socket having an inner diameter which is sufficient to allow engagement of said proximal end of said medical device; and driving means forming an integral part of and disposed at said cylindrical member driving end for driving said locking cap into said bone.

2. A locking cap as recited in claim 1, wherein said socket has helical inner threads with an inner thread pitch on its inner surface.

3. A locking cap as recited in claim 2, wherein said cylindrical member outer thread pitch and said socket inner thread pitch are like-handed.

4. A locking cap as recited in claim 2, wherein said cylindrical member outer thread pitch and said socket inner thread pitch are opposite-handed.

5. A locking cap as recited in claim 2, wherein said cylindrical member outer thread pitch is greater than said socket inner thread pitch.

6. A locking cap as recited in claim 5, wherein a ratio of said cylindrical member outer thread pitch to said socket inner thread pitch is at least 2:1.

7. A locking cap as recited in claim 2, wherein said cylindrical member outer thread pitch is less than said socket inner thread pitch.

8. A locking cap as recited in claim 1, wherein said outer threads have leading and trailing edge with cutting flutes.

9. A locking cap as recited in claim 1 further comprising a hole disposed within said cylindrical member driving end and said hole connecting to said socket, whereby said hole provides access to said socket for a set screw to engage said proximal end of said medical device.

10. A locking cap as recited in claim 1, wherein said driving means comprises a tool interface for cooperatively engaging a driving tool.

11. A locking cap as recited in claim 10, wherein said tool interface comprises a hexagonal socket for receiving a hexagonal wrench tip.

12. A locking cap as recited in claim 1, wherein said cylindrical member has an outer diameter substantially within the range of 1.25-25 mm, and said cylindrical socket inner diameter is substantially within the range of 1-24.5 mm.

13. A locking cap as recited in claim 1, wherein said locking cap is substantially fabricated from a physiologically compatible material selected from the group consisting of cobalt chrome, titanium, stainless steel, ceramic materials, resorbable materials, and composite materials.

14. A locking cap as recited in claim 1 further comprising an elongate cylindrical shaft connecting said cylindrical member driving end to said socket within said cylindrical member driven end, said shaft being concentrically disposed within said cylindrical member and said shaft having an inner diameter which is sufficient to allow passage of said proximal end of said medical device.

15. A locking cap as recited in claim 14, wherein said socket has helical inner threads with an inner thread pitch on its inner surface.

16. A locking cap as recited in claim 15, wherein said cylindrical member outer thread pitch and said socket inner thread pitch are like-handed.

17. A locking cap as recited in claim 15, wherein said cylindrical member outer thread pitch and said socket inner thread pitch are opposite-handed.

18. A locking cap as recited in claim 15, wherein said cylindrical member outer thread pitch is greater than said socket inner thread pitch.

19. A locking cap as recited in claim 18, wherein a ratio of said cylindrical member outer thread pitch to said socket inner thread pitch is at least 2:1.

20. A locking cap as recited in claim 15, wherein said cylindrical member outer thread pitch is less than said socket inner thread pitch.

21. A locking cap as recited in claim 14, wherein said driving means comprises a tool interface for cooperatively engaging a driving tool.

22. A locking cap as recited in claim 21, wherein said tool interface comprises a peripheral surface for receiving a wrench.

23. A locking cap as recited in claim 14, wherein said cylindrical member has an outer diameter substantially within the range of 1.25-25 mm, and said cylindrical socket inner diameter is substantially within the range of 1-24.5 mm.

24. A locking cap as recited in claim 14, wherein said locking cap is substantially fabricated from a physiologically compatible material selected from the group consisting of cobalt chrome, titanium, stainless steel, ceramic materials, resorbable materials, and composite materials.

25. An osteal implant for anchoring an implanted medical device within a bone by engaging a proximal end of said device and fastening said implant to a bone, comprising:

an elongate cylindrical member having helical outer threads about its cylindrical periphery, a driving end and a driven end, said outer threads having an outer thread pitch;

an elongate cylindrical threaded socket for receiving said proximal end of said medical device, said socket being concentrically disposed within said cylindrical member driven end and said socket having an inner diameter which is sufficient to allow engagement of said proximal end of said medical device, and wherein said cylindrical member outer thread pitch and said socket inner thread pitch are like-handed, and said cylindrical member outer thread pitch is greater than said socket inner thread pitch; and driving means disposed at said cylindrical member driving end for driving said implant into said bone.

26. An implant as recited in claim 25, wherein a ratio of said cylindrical member outer thread pitch to said socket inner thread pitch is at least 2:1.

27. An implant as recited in claim 25, wherein said cylindrical member outer threads have leading and trailing ends with cutting flutes.

28. An implant as recited in claim 25, wherein said driving means comprises a tool interface for cooperatively engaging a driving tool.

29. An implant as recited in claim 28, wherein said tool interface comprises a hexagonal socket for receiving a hexagonal wrench tip.

30. An implant as recited in claim 25, wherein said cylindrical member has an outer diameter substantially within the range of 1.25-25 mm, and said cylindrical socket inner diameter is substantially within the range of 1-24.5 mm.

31. An implant as recited in claim 25, wherein said implant is substantially fabricated from a physiologically compatible material selected from the group consisting of cobalt chrome, titanium, stainless steel, ceramic materials, resorbable materials, and composite materials.

32. An implant as recited in claim 25 further comprising an elongate cylindrical shaft connecting said cylindrical member driving end to said socket within said cylindrical member driven end, said shaft being concentrically disposed within said cylindrical member and said shaft having an inner diameter which is sufficient to allow passage of said proximal end of said medical device.

33. An implant as recited in claim 32, wherein a ratio of said cylindrical member outer thread pitch to said socket inner thread pitch is at least 2:1.

34. An implant as recited in claim 32, wherein said cylindrical member outer threads have leading and trailing ends with cutting flutes.

35. A locking cap as recited in claim 32, wherein said driving means comprises a tool interface for cooperatively engaging a driving tool.

36. A locking cap as recited in claim 35, wherein said tool interface comprises a peripheral surface for receiving a wrench.

37. An implant as recited in claim 32, wherein said cylindrical member has an outer diameter substantially within the range of 1.25-25 mm, and said cylindrical socket inner diameter is substantially within the range of 1-24.5 mm.

38. An implant as recited in claim 32, wherein said implant is substantially fabricated from a physiologically compatible material selected from the group consisting of cobalt chrome, titanium, stainless steel, ceramic materials, resorbable materials, and composite materials.

39. An osteal implant for anchoring an implanted medical device within a bone by engaging a proximal end of said device and fastening said implant to a bone, comprising:

an elongate cylindrical member having helical outer threads about its cylindrical periphery, a driving end and a longitudinally opposed driven end, said outer threads having an outer thread pitch;

an elongate cylindrical threaded socket for receiving said proximal end of said medical device, said socket being concentrically disposed within said cylindrical member driven end and said socket having an inner diameter which is sufficient to allow engagement of said proximal end of said medical device;

a hole disposed within said cylindrical member driving end and said hole connecting to said socket, whereby said hole provides access to said socket for a set screw to engage said proximal end of said medical device; and driving means forming an integral part of and disposed at said cylindrical member driving end for driving said implant into said bone.

40. An implant as recited in claim 39, wherein said cylindrical member outer threads have leading and trailing ends with cutting flutes.

41. An implant as recited in claim 39, wherein said driving means comprises a tool interface for cooperatively engaging a driving tool.

42. An implant as recited in claim 41, wherein said tool interface comprises a hexagonal socket for receiving a hexagonal wrench tip.

43. An implant as recited in claim 39, wherein said cylindrical member has an outer diameter substantially within the range of 1.25-25 mm, and said cylindrical socket inner diameter is substantially within the range of 1-24.5 mm.

44. An implant as recited in claim 39, wherein said implant is substantially fabricated from a physiologically compatible material selected from the group consisting of cobalt chrome, titanium, stainless steel, ceramic materials, resorbable materials, and composite materials.

* * * * *